(12) United States Patent
Wollenweber

(10) Patent No.: US 6,590,213 B2
(45) Date of Patent: Jul. 8, 2003

(54) METHOD AND SYSTEM FOR ESTIMATING SCATTER IN A PET SCANNER

(75) Inventor: Scott D. Wollenweber, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 173 days.

(21) Appl. No.: 09/949,074

(22) Filed: Sep. 7, 2001

(65) Prior Publication Data
US 2003/0047687 A1 Mar. 13, 2003

(51) Int. Cl.[7] .............................................. G01T 1/166
(52) U.S. Cl. ............................ 250/363.03; 250/363.02
(58) Field of Search ....................... 250/363.03, 363.02, 250/363.04, 363.07, 369, 370.09

(56) References Cited

U.S. PATENT DOCUMENTS

| | | | |
|---|---|---|---|
| 5,241,181 A | | 8/1993 | Mertens et al. |
| 5,272,343 A | | 12/1993 | Stearns |
| 5,600,144 A | * | 2/1997 | Worstell ................. 250/363.03 |
| 6,429,434 B1 | * | 8/2002 | Watson et al. .......... 250/363.04 |
| 6,462,342 B1 | * | 10/2002 | Stearns .................. 250/363.03 |
| 6,490,476 B1 | * | 12/2002 | Townsend et al. .......... 600/427 |

OTHER PUBLICATIONS

Ollinger, John M., "Model–based scatter correction for fully 3D PET," Phys.Med. Biol. 41 (1996), pp 153–176, printed in the UK.
Watson, C.C., "New, Faster, Image–Based Scatter Correction for 3D PET," IEEE MIC 1999, M 11–5.
Watson, C.C., "Evaluation of Simulation–Based Scatter Correction for 3–D PET Cardiac Imaging," IEEE Trans. On Nucl. Science, vol. 44, No. 1, Feb. 1997, pp. 90–97.

* cited by examiner

Primary Examiner—Constantine Hannaher
Assistant Examiner—Otilia Gabor
(74) Attorney, Agent, or Firm—Quarles & Brady LLP; Carl Horton (57) ABSTRACT

A method of processing an image data set of a 3D PET scanner to correct for scattered coincidence events, as well as a 3D PET scanner, are disclosed. The method of processing the image data set includes providing an image data set including a first plurality of data subsets respectively corresponding to a plurality of native slices. The method additionally includes axially downsampling the first plurality of data subsets to generate a second plurality of data subsets respectively corresponding to a plurality of superslices. The method further includes calculating scatter in the second plurality of data subsets by way of a model-based scatter correction algorithm.

20 Claims, 5 Drawing Sheets

NATIVE 35 AXIAL SLICE DATA ← AXIAL

METHOD AND SYSTEM FOR ESTIMATING SCATTER IN A PET SCANNER

BACKGROUND OF THE INVENTION

The field of the invention is positron emission tomography (PET) scanners, and particularly PET scanners that can acquire data in a three-dimensional (3D) mode.

Positrons are positively charged electrons which are emitted by radionuclides that have been prepared using a cyclotron or other device. These are employed as radioactive tracers called "radiopharmaceuticals" by incorporating them into substances, such as glucose or carbon dioxide. The radiopharmaceuticals are injected in the patient and become involved in such processes as blood flow, fatty acid, glucose metabolism, and protein synthesis. As the radionuclides decay, they emit positrons. The positrons travel a very short distance before they encounter an electron, and when this occurs, they are annihilated and converted into two photons, or gamma rays. This annihilation is characterized by two features which are pertinent to PET scanners—each gamma ray has an energy of 511 keV and the two gamma rays are directed in nearly opposite directions. An image is created by determining the number of such annihilations at each location within the field of view.

A typical PET scanner is cylindrical and includes a detector ring assembly composed of rings of detectors which encircle the patient and which convert the energy of each 511 keV photon into a flash of light that is sensed by a photomultiplier tube (PMT). Coincidence detection circuits connect to the detectors and record only those photons which are detected simultaneously by detectors located on opposite sides of the patient. The number of such simultaneous events (coincidence events) indicates the number of positron annihilations that occurred along a line joining the two opposing detectors. During an acquisition, coincidence events are recorded to indicate the number of annihilations along lines joining pairs of detectors in the detector ring. These numbers are employed to reconstruct an image using well-known computed tomography techniques.

When originally developed, PET scanners were strictly multiplanar scanners. In such PET scanners, each detector ring is configured to detect annihilations occurring only within the plane of that respective ring alone, or at most within planes defined by detectors on adjacent rings, and not annihilations occurring at other positions within the PET scanner. Because each detector within each detector ring is capable of receiving photons coming in toward the detector from a variety of angles (rather than merely coming in toward the detector from the center of the ring of which the detector is a part), fixed slice septa are positioned in between each of the detector rings of the PET scanners for imaging in what is known as "2D mode". The septa, which are commonly composed of lead or tungsten alloy, shield the detectors of each individual detector ring from photons that have not originated from annihilations within the plane defined by the detector ring. The septa further have the function of shielding the detectors of the detector rings from out-of-plane scattered photons or other photons that are not resulting from annihilations (i.e., photons entering at either end of the cylindrical PET scanner).

A major innovation in PET scanners that occurred in the late 1980s and early 1990s has been the development of 3D PET scanners, which include true-3D (or "volumetric") PET scanners and pseudo-3D PET scanners. In contrast to multiplanar scanners, true-3D PET scanners have no septa and consequently the detectors of each detector ring of the scanners can receive photons from a wider range of angles with respect to the plane of the respective ring than in multiplanar PET scanners. Although pseudo-3D PET scanners do employ septa, the septa are short so as to primarily reduce out of field-of-view (FOV) scatter. 3D PET scanners became feasible partly as a result of the increased speed of computers, since PET imaging in such scanners requires determining the existence of, and processing information related to, coincidence events that occur not merely between pairs of detectors positioned on individual (or adjacent) detector rings, but also between pairs of detectors positioned on different detector rings (or different detector rings that are spaced more than one ring apart from one another). 3D PET scanners allow for increased sensitivity relative to multiplanar scanners, since more true coincidence events can be recorded. However, 3D PET scanners also admit more scattered and random coincidence events to the data set from which the image is reconstructed than multiplanar PET scanners. In particular, scattered coincidence events can account for more than 50% of recorded coincidence events in the case of procedures such as torso imaging.

To address the problem of correcting for scatter in 3D PET scanners, model-based scatter correction methods have been proposed. Model-based scatter correction methods generally involve algorithms that use the acquired PET emission and transmission data to form a set of images, downsample the data to reduce the number of pixels, determine contributed-to detector pairs and calculate the expected flux of single-scatter radiation that is detected in different lines-of-response between different detectors. One such model-based scatter correction method was set forth in an article by John M. Ollinger entitled "Model-Based Scatter Correction for Fully 3D-PET" (Phys. Med. Biol. 41, pages 153–176, 1996), which is hereby incorporated by reference herein. Another model-based scatter correction method was set forth in an article by C. C. Watson entitled "New, Faster, Image-Based Scatter Correction for 3D-PET" (IEEE Trans. Nucl. Sci., 44, 90–97, 1997), which also is hereby incorporated by reference herein.

The aforementioned model-based scatter correction methods are pixel (or voxel) driven routines and that use measured data as the inputs. To obtain output results that are based mainly upon true coincidence event data and not scattered coincidence events, the model-based scatter correction methods involve performing multiple iterations of the scatter estimation, where each iteration involves nested looping through several dimensions. For example, the model-based scatter correction method set forth by Ollinger involves processing the data set obtained by the PET scanner by looping through such dimensions as the transaxial distance, the theta angle (angular orientation within a particular detector ring with respect to horizontal) and the azimuthal angle (angular orientation between different detector rings). The model-based scatter correction method set forth by Watson proceeds in a similar manner.

Because of the iterative nature of model-based scatter correction methods, and particularly the nested looping through multiple parameters that is performed according to those methods, the model-based scatter correction methods are limited in their usefulness in conventional 3D PET scanners insofar as the methods employ intensive processing. For example, to perform the first of the above-identified model-based scatter correction methods, nested looping is performed over several parameters, including a first parameter concerning the detector hit by an unscattered photon (d1), a second parameter concerning azimuthal angle, a third parameter concerning in-transverse-plane angle, a fourth parameter concerning the transverse distance across the image pixels, a fifth parameter concerning the transverse distance down the image pixels away from the detector d1 (defined scatter voxel S), and a sixth parameter concerning detectors contributed to for scatter voxel S. Typically, in order to perform three iterations of these nested loops for this model-based scatter correction method using a conventional Sun Ultra-Sparc 360 MHz processor, up to 8–12 minutes of processing time is required.

Because of the continuing need for improvements in the speed and accuracy with which 3D PET images can be produced, it would therefore be advantageous if a method and system was developed in PET scanners that allowed scatter to be corrected in a more rapid, less processing-intensive manner than currently exists.

BRIEF SUMMARY OF THE INVENTION

The present inventor has discovered that it is possible to improve the speed of execution of model-based scatter algorithms by combining axial data within certain ranges into composite transaxial planes or "super-slices" and thus effectively collapsing data along the axial direction. By so combining the axial data, one can perform the model-based scatter algorithms by looping over the in-plane parameters x and y within each super-slice, instead of looping over both the in-plane parameters and the azimuthal angle dimension. By eliminating the calculations associated with looping over the azimuthal angle dimension, the computation time required for performing the method-based scatter algorithms is reduced.

The present invention relates to a method of processing an image data set of a 3D PET scanner to correct for scattered coincidence events, where the 3D PET scanner includes a detector ring assembly having a central axis. The method of processing the image data set includes providing an image data set including a first plurality of data subsets respectively corresponding to a plurality of native slices. The method additionally includes axially downsampling the first plurality of data subsets to generate a second plurality of data subsets respectively corresponding to a plurality of super-slices. The method further includes calculating scatter in the second plurality of data subsets by way of a model-based scatter correction algorithm.

The present invention additionally relates to a method of processing an image data set of a 3D PET scanner to correct for scattered coincidence events, where the 3D PET scanner includes a detector assembly having a central axis. The method includes (a) providing an emission image data set and transmission image data set, where the emission image data set includes a plurality of emission data subsets respectively corresponding to a plurality of native slices, and where the transmission image data set includes a plurality of transmission data subsets respectively corresponding to the plurality of native slices. The method further includes (b) axially downsampling the plurality of emission data subsets to generate an axially downsampled emission data set corresponding to at least one super-slice, and axially downsampling the plurality of transmission data subsets to generate an axially downsampled transmission data set corresponding to the at least one super-slice. The method additionally includes (c) transaxially downsampling each of the axially downsampled emission data set and the axially downsampled transmission data set to generate a downsampled emission data set and a downsampled transmission data set. The method further includes (d) calculating scatter based upon the downsampled emission and transmission data sets to generate a scatter sinogram data set, and (e) repeating (c)–(d) until scatter has been adequately calculated as determined according to a convergence rule.

The present invention additionally relates to a 3D PET scanner that includes a gantry, a plurality of sets of detectors supported by the gantry, and a processing means. The detectors in each set are disposed in a plane and positioned about a central axis that intersects the plane, and the sets of detectors are spaced along the central axis. Each set of detectors forms respective a native axial slice. The processor means is for providing an image data set including a first plurality of data subsets respectively corresponding to the respective native slices. The processor means additionally is for axially downsampling the first plurality of data subsets to generate a second plurality of data subsets respectively corresponding to a plurality of super-slices. The processor means further is for calculating scatter in the second plurality of data subsets by way of a model-based scatter correction algorithm.

DESCRIPTION OF THE PREFERRED EMBODIMENT

Figure 1:
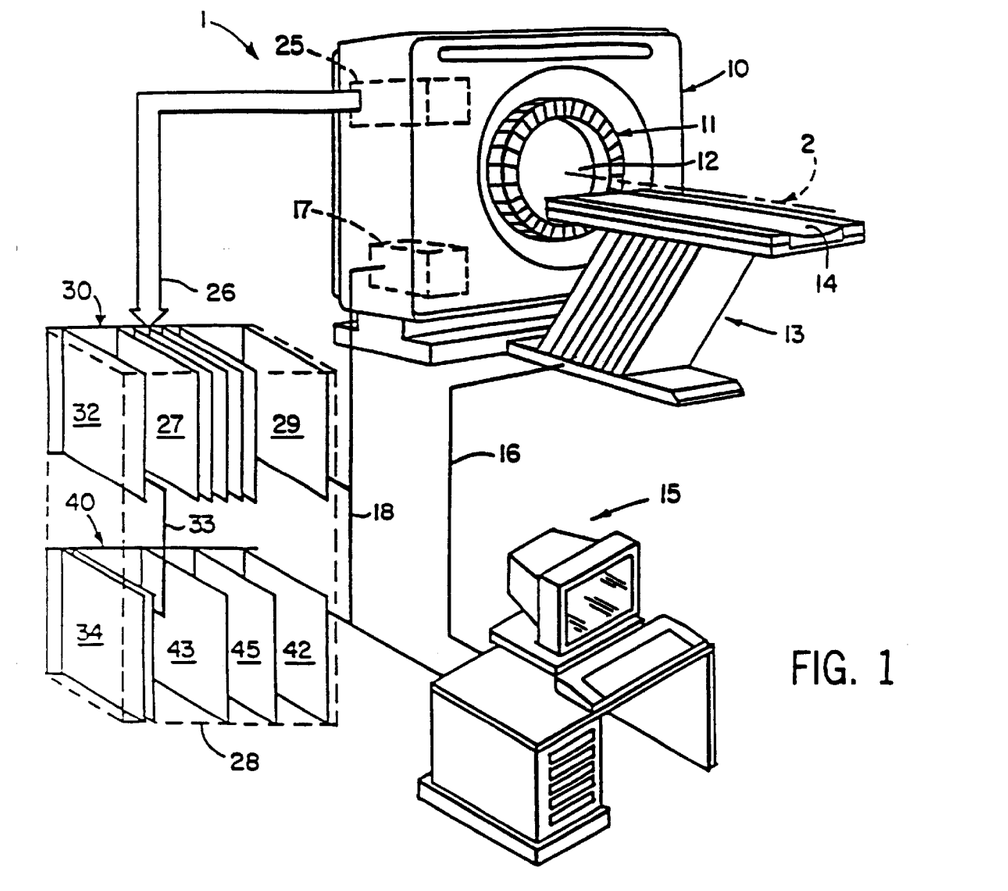
FIG. 1 is a pictorial view with parts cut away of a 3D PET scanner that employs the present invention.

Referring particularly to FIG. 1, a 3D PET scanner 1 is shown. The 3D PET scanner 1, which is representative of both true-3D (or volumetric) PET scanners and pseudo-3D PET scanners, includes a gantry 10 which supports a detector ring assembly 11 about a central opening, or bore 12. The detector ring assembly 11 is circular in shape, and is made up of multiple detector rings (not shown) that are spaced along a central axis 2 to form a cylindrical detector ring assembly. A patient table 13 is positioned in front of the gantry 10 and is aligned with the central axis 2 of the detector ring assembly 11. A patient table controller (not shown) moves the table bed 14 into the bore 12 in response to commands received from an operator workstation 15 through a serial communications link 16. A gantry controller 17 is mounted within the gantry 10 and is responsive to commands received from the operator workstation 15 through a local area network 18 to operate the gantry.

Figure 2:
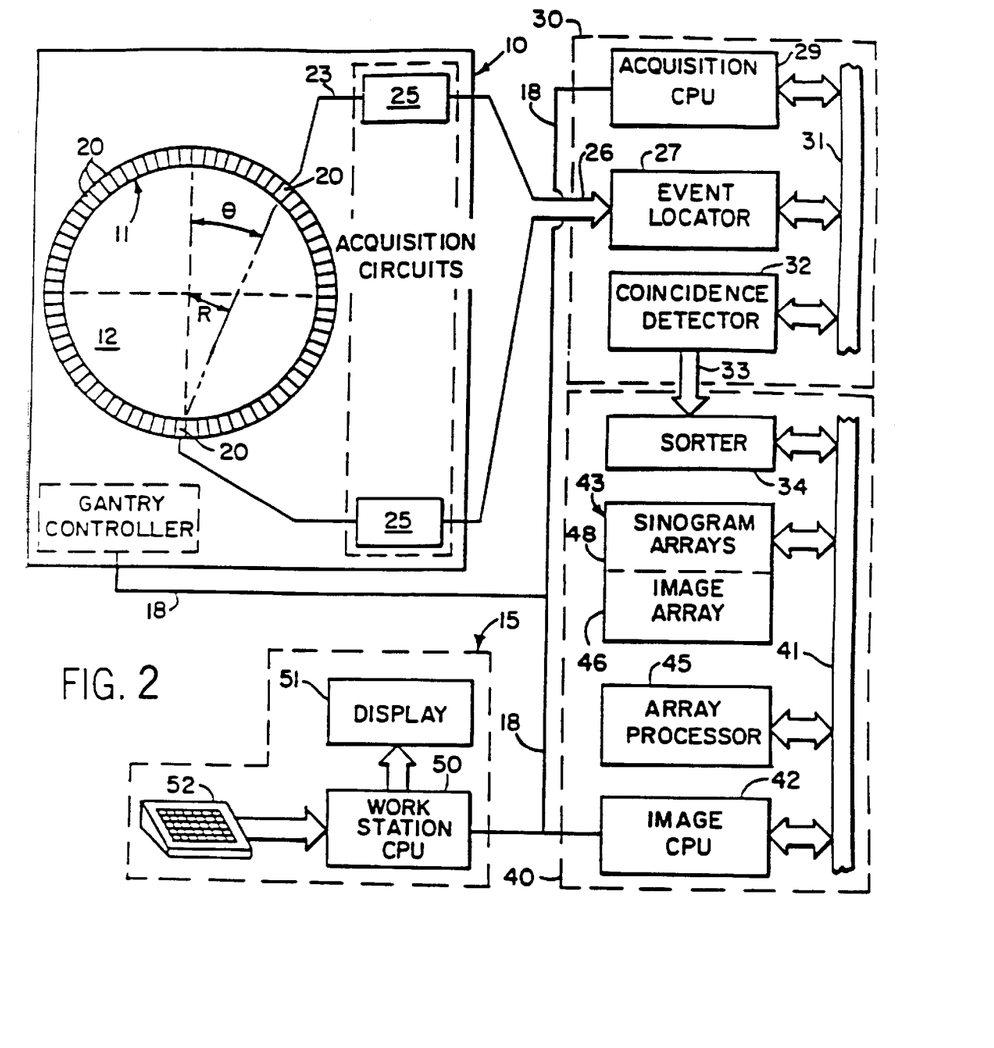
FIG. 2 is a schematic diagram of the 3D PET scanner of FIG. 2.
Figure 3:
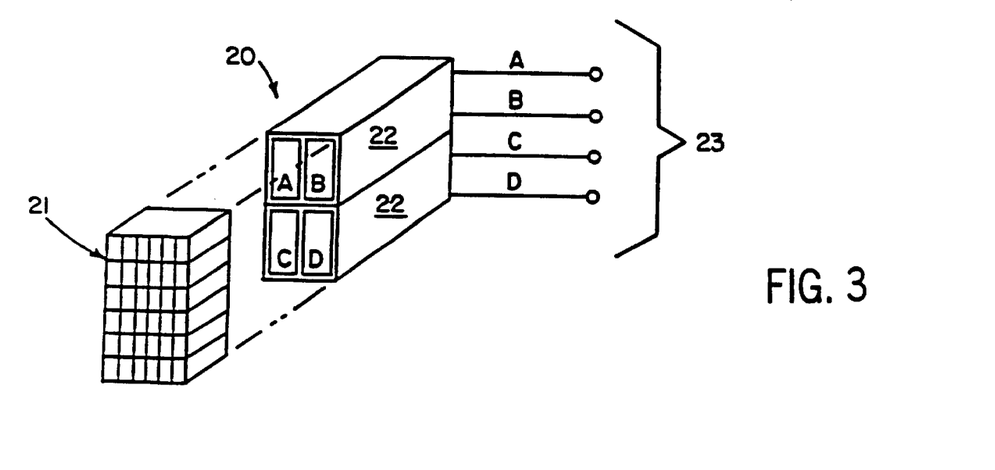
FIG. 3 is a pictorial view of a detector that forms part of the 3D PET scanner of FIG. 1.

As shown best in FIGS. 2 and 3, each detector ring of the detector ring assembly 11 is comprised of detectors 20. Each detector 20 includes a scintillator or BGO crystal 21. Each BGO crystal 21 is disposed in front of a photomultiplier tube 22 (abbreviated PMT). More than one BGO crystal 21 can be disposed in front of a given PMT 22. For example, in one embodiment (shown in FIG. 3) a matrix of thirty-six BGO crystals 21 is disposed in front of four PMTs 22, such that nine BGO crystals are disposed in front of each of the PMTs. All of the PMTs 22 produce analog signals on line 23 when a scintillation event occurs at one of the respective nine BGO crystals 21 that are disposed in front of the PMTs (i.e., when a photon is received by one of the BGO crystals 21). A set of acquisition circuits 25 is mounted within the gantry 10 to receive these signals and produce digital signals indicating the event coordinates (x,y,z) and the total energy. These are sent through a cable 26 to an event locator circuit 27 housed in a separate cabinet 28. Each acquisition circuit 25 also produces an event detection pulse (EDP), which indicates the exact moment the scintillation event took place.

Referring particularly to FIGS. 2 and 3, the event locator circuits 27 form part of a data acquisition processor 30 that periodically samples the signals produced by the acquisition circuits 25. The processor 30 has an acquisition CPU 29 that controls communications on the local area network 18 and a backplane bus 31. The event locator circuits 27 assemble the information regarding each valid event into a set of digital numbers that indicate precisely when the event took place and the position of the detector 20/crystal 21 which detected the event. This event data packet is conveyed to a coincidence detector 32, which is also part of the data acquisition processor 30.

The coincidence detector 32 accepts the event data packets from the event locators 27 and determines if any two of them are in coincidence. Coincidence is determined by a number of factors. First, the time markers in each event data packet must be within a specified time window of each other, and second, the locations indicated by the two event data packets must lie between a pair of detectors which have a line-of-response which passes through the field of view (FOV) in the scanner bore 12. Events which cannot be paired as such are discarded, but coincident event pairs are located and recorded as a coincidence data packet that is conveyed through a serial link 33 to a sorter 34. For a detailed description of the coincidence detector 32, reference is made to U.S. Pat. No. 5,241,181 entitled "Coincidence Detector For A PET Scanner" which is incorporated herein by reference.

The sorter 34 forms part of an image reconstruction processor 40. The sorter 34 counts all events occurring along each projection ray and organizes them into a two dimensional sinogram array 48 which is stored in a memory module 43. The image reconstruction processor 40 also includes an image CPU 42 that controls a backplane bus 41 and links it to the local area network 18. An array processor 45 also connects to the backplane bus 41 and it reconstructs images from the sinogram arrays 48. The resulting image array 46 is stored in memory module 43 and is output by the image CPU 42 to the operator work station 15. For a detailed description of the sorter 34, reference is made to U.S. Pat. No. 5,272,343 entitled "Sorter For Coincidence timing Calibration In A PET Scanner" which is incorporated herein by reference.

The operator workstation 15 includes a CPU 50, a CRT display 51 and a keyboard 52. The CPU 50 connects to the local area network 18 and it scans the keyboard 52 for input information. Through the keyboard 52 and associated control panel switches, the operator can control the calibration of the PET scanner, its configuration, and the positioning of the patient table for a scan. Similarly, the operator can control the display of the resulting image on the CRT display 51 and perform image enhancement functions using programs executed by the workstation CPU 50.

Figure 4:
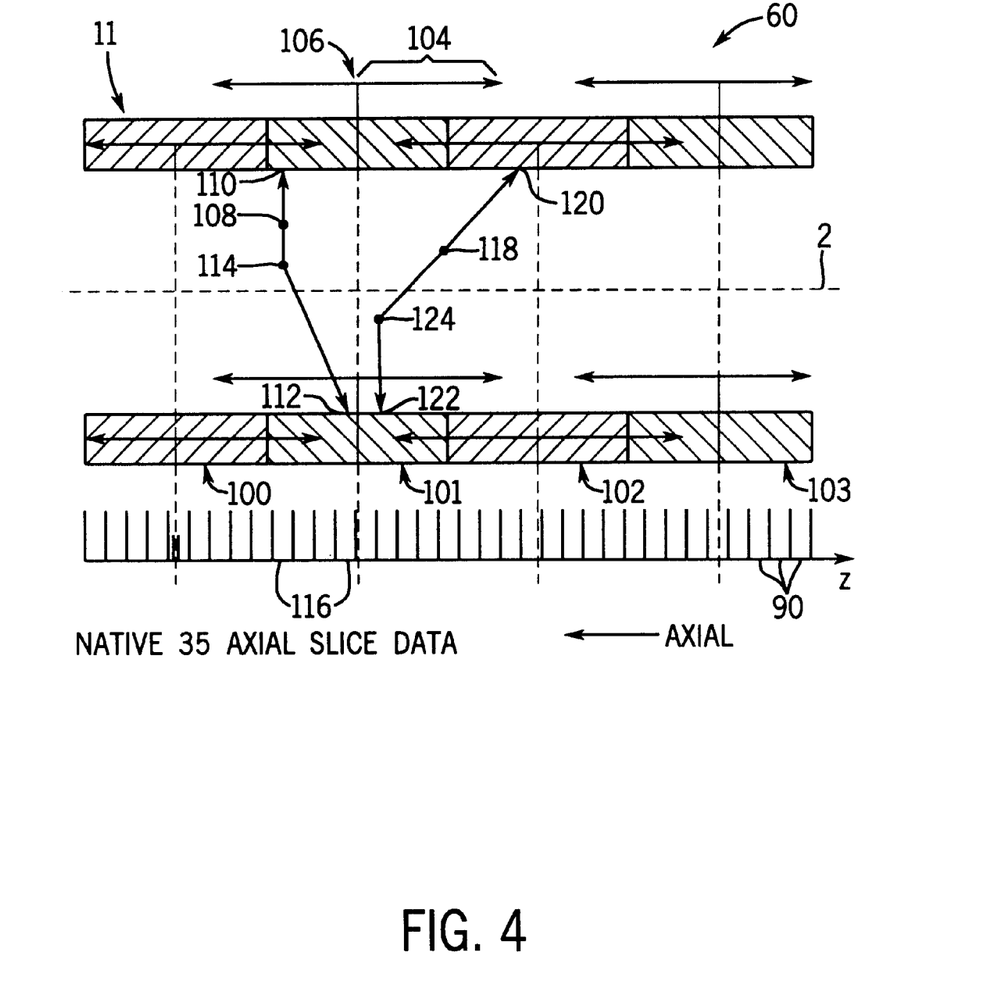
FIG. 4 is a schematic diagram of a cross-section through the detector ring assembly of the 3D PET scanner of FIG. 1, taken along the central axis of the detector ring assembly, in which native slices are correlated with super-slices.
Figure 5:
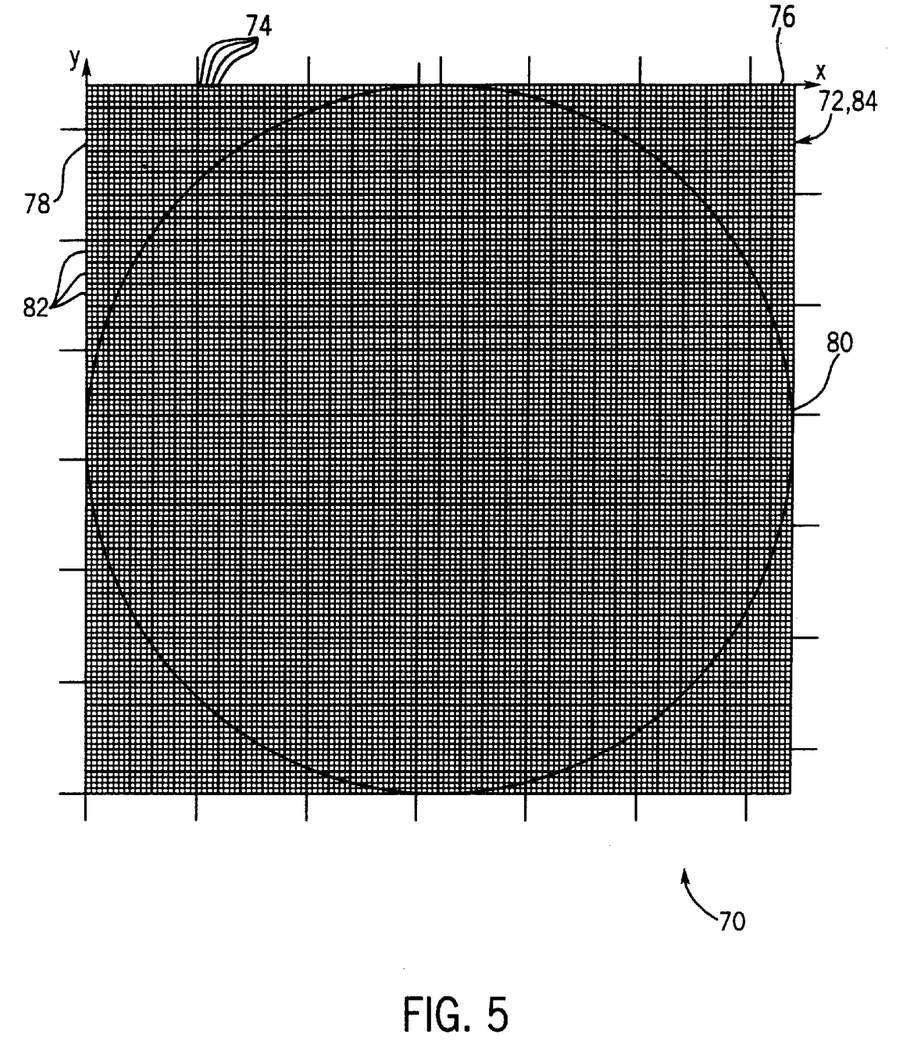
FIG. 5 is a schematic diagram of a cross-section through the detector ring assembly of the 3D PET scanner of FIG. 1, which shows the correlation between native pixels and downsampled pixels.

Turning to FIGS. 4 and 5, first and second cross-sectional views 60, 70 of the detector ring assembly 11 are provided. More specifically, the first and second cross-sectional views 60, 70 are taken, respectively, along the central axis 2 and perpendicular to the central axis through one of the detector rings 80. In the present embodiment of the 3D PET scanner 1, there are eighteen detector rings 80. Because the 3D PET scanner identifies as transaxial planes both the planes formed by detector rings and planes formed between adjacent rings, the 3D PET scanner includes thirty-five transaxial planes or native axial slices 90. FIG. 5 further illustrates the concept of image downsampling as employed by the 3D PET scanner 1. As shown, a native image 72 initially includes 128×128 pixels 74 formed by 128 divisions along each of x and y axes 76, 78, respectively. During image processing by the image reconstruction processor 40, information associated with the pixels 74 within respective groupings 82 of the 128×128 pixels 74 are added to produce a 32×32 pixel image 84.

Referring still to FIG. 4, in accordance with one embodiment of the present invention, model-based scatter correction methods such as those discussed above can be more efficiently employed by axially downsampling coincidence data received at the thirty-five native axial slices 90 to generate four axial composite planes or "super-slices" 100, 101, 102 and 103. By axial downsampling the coincidence data, overall tallies for scattered coincidence events are only generated for the super-slices 100–103 rather than for each individual native axial slice 90. In alternate embodiments, the native axial slices 90 can include a greater or lesser number of slices than the thirty-five slices shown in FIG. 4, and/or the native axial slices can form a different number of super-slices other than the four super-slices shown in FIG. 4. Also, in certain embodiments, the number of native axial slices 90 that form the different super-slices need not be the same for each of the different super-slices. Typically, the number of native axial slices 90 that form a single super-slice will be in the range of 4 to 7 slices, for a detector ring assembly having thirty-five native axial slices as in the present embodiment.

Although the number of slices for which scattered coincidence event data is generated is determined by the number of super-slices 100–103, the determination as to which of the scattered coincidence event data is used to generate the scattered coincidence event data for each super-slice depends upon an axial extent 104 associated with each of the super-slices 100–103. The axial extent 104 is defined as a distance extending from a center 106 of each super-slice (e.g., the super-slice 101) within which to include scattered coincidence event data for the respective super-slice. For example, if the axial extent is 5.0 cm, then data within a 10 cm range of the center of the super-slice is used to determine the super-slice data.

Typically, the axial extent is greater than half the physical width of the corresponding super-slice, to allow for some axial overlapping in (and blurring of) the scattered coincidence event data that is associated with each super-slice. It has been determined experimentally that typical distributions of scattered coincidence events are low-frequency (e.g., blurred), such that large super-slices with large axial extents can be employed. However, the axial extent can vary depending upon the embodiment. In certain embodiments, the axial extent for each super-slice can vary with the different super-slices, and the axial extent for a given super-slice can be asymmetric on opposite sides of the center of that super-slice. Also depending upon the embodiment, weighting functions can be applied to the scattered coincidence event data as a function of distance from the centers of the super-slices to influence the determined scatter distributions.

By axially downsampling the scattered coincidence event data, the amount of scattered coincidence event data that must be interpreted to account for scattering is reduced. For example, as shown in FIG. 4, without the combination of coincidence data into super-slices, an annihilation event 108 producing a first photon 110 and a scattered photon 112 scattered at a scattering point 114 would be registered as a coincidence event occurring between two different detector rings 116, while with the combination of coincidence data into super-slices, the annihilation is registered as a coincidence event occurring within the same super-slice 101. This is not to say that all coincidence events will occur within the same super-slice. For example, another annihilation event 118 also shown in FIG. 4 produces a first photon 120 and a scattered photon 122 scattered at a scattering point 124, and is registered as a coincidence event occurring within neighboring super-slices 101 and 102 (since the first photon 120 impinges a detector ring beyond the axial extent 104 of the super-slice 101 and the scattered photon 122 impinges a detector ring beyond the axial extent of the super-slice 102).

Figure 6:
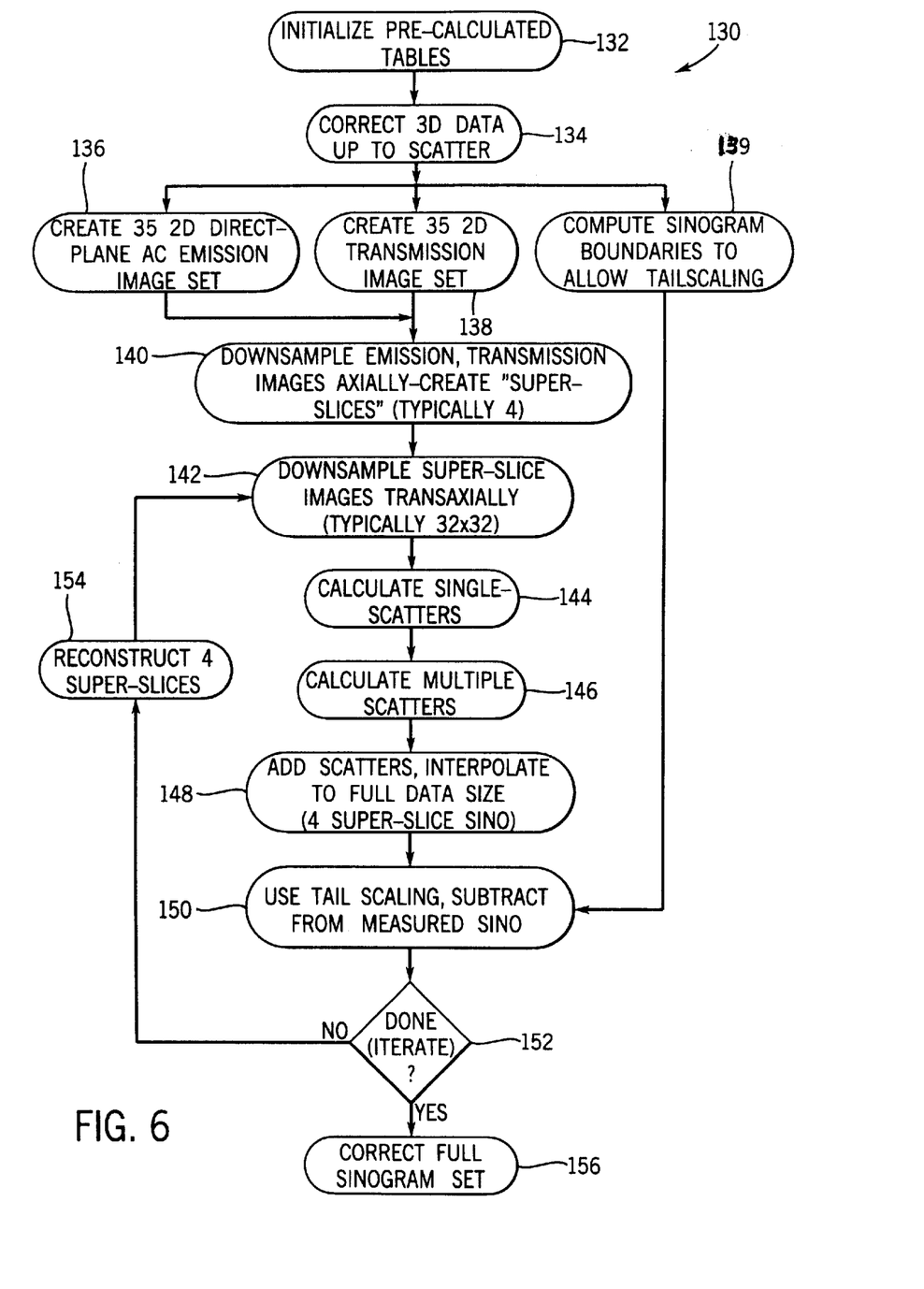
FIG. 6 is a flow chart showing exemplary method steps performed by one embodiment of the 3D PET scanner of FIG. 1 in correcting for scatter.

Turning to FIG. 6, a flow chart 130 shows exemplary method steps of the image reconstruction processor 40 and particularly the array processor 45 in performing a model-based scatter correction method that employs axial downsampling by way of super-slices as discussed above. As shown, in steps 132 and 134, respectively, pre-calculated tables are generated and 3D coincidence event data obtained from the sorter 34 is corrected for error other than that due to scatter. Then, at steps 136 and 138, an attenuation corrected ("AC") emission image data set and a transmission image data set are generated based upon the corrected 3D coincidence event data. Each of the emission and transmission image data sets include subsets of data corresponding respectively to each of the thirty-five native axial slices 90. Also, each of these subsets of data is 2D (two-dimensional) rather than 3D, such that each data point is referenced with respect to only the x and y. Additionally, at step 139, sinogram boundaries are calculated, based upon the corrected 3D coincidence event data, to allow for tail-scaling.

Next, at step 140, the emission and transmission 2D image data sets developed at steps 136 and 138 are axially downsampled to generate emission and transmission image data sets corresponding to the super-slices 90, which also are 2D. For example, the 2D emission data subsets for a first seven of the native axial slices 90 are summed together (or otherwise combined) to form the overall 2D emission data subset for the first super-slice 100. Upon the generation of super-slice image data sets, the model-based scattering correction method can process the information in the same manner to account for, and reduce the effects of, scatter as would be the case in conventional systems. However, because of the generation of the super-slice image data sets, the scattered coincidence events need not be accounted for between each of the thirty-five native axial slices 90, but rather can be accounted for between the four axial super-slices 100–103. Thus, the model-based scatter correction method need not loop through thirty-five values of the axial dimension (z), but can merely loop through calculating four values of the axial dimension corresponding to the four super-slices 100–103.

Thus, at step 140, the super-slice image data sets are downsampled transaxially as discussed with regard to FIG. 5, so as to reduce the number of pixels along each of the x and y dimensions from 128 to 32 (in one embodiment). Next, at step 144, single scatter events are calculated. In order to perform these calculations, the image data set information, in which pixel locations are defined with reference to the x and y axes 76, 78, is used to generate a scatter sinogram, in which locations are defined with respect to a central axis by way of a distance variable (R) and an angular variable ($\theta$) as shown in FIG. 2. Due to the transaxial downsampling of the image data sets with respect to the x and y dimensions, the number of possible gradations of the sinogram in terms of the distance variable (R) and the angular variable ($\theta$) are also reduced to a smaller number (e.g., 27 by 32) than in the case of a sinogram where downsampling was not performed (e.g., 281 by 336).

The calculating of the single scatters at step 144 refers to the estimating of the contribution, to the overall numbers of detected coincidence events, of pairs of photons in which one of the photons has been scattered one time following the annihilation event (e.g., as shown in FIG. 4). The single scatters for each sinogram are calculated using information provided by the sinogram and emission image data set and the sinogram and image corresponding to the transmission data set. Although single scatters are the most common type of scatters, multiple scatters also can occur, in which both photons from an annihilation event are scattered once or more than once, or one of the photons from an annihilation event is scattered more than once. Consequently, at step 146, multiple scatter contributions to the overall numbers of detected coincidence events are also calculated. Typically, the multiple scatters are calculated at least in part based upon the single scatters calculated at step 144. The calculating of single and multiple scatters in steps 144, 146 forms part of an overall conversion of the data from image format into sinogram format.

Once both the single scatters and multiple scatters have been calculated, all of the scatter contributions are added and a corrected sinogram is obtained, at step 148. The step 148 includes the interpolation of the corrected sinogram back from the transaxially downsampled size (e.g., 27 by 32) to a normal size (e.g., 281 by 336). This interpolation also includes interpolation of the data back from data sets corresponding to the super-slices 100–103 to data sets corresponding to the native axial slices 90. Once the corrected, normal-sized set of sinograms is generated, tail scaling is performed at step 150 by using information provided by the sinogram boundaries generated at step 139 from the corrected, normal-sized sinogram. The tail scaling operation sets the magnitude of the desired scatter correction by allowing calculation of the ratio of counts outside a given measured emission sinogram boundary to that in the scatter sinogram estimate. It is assumed that counts eminating from outside the object (determined by step 139) are scatter.

At step 152, it is then determined whether scatter has been adequately accounted for by operation of the model-based scatter correction method or whether the algorithm must be performed another time. Typically, a convergence rule is used to make this determination, such that it is determined whether the scatter calculations have converged sufficiently. If it is determined that the algorithm must iterate, the sinogram data is reconstructed from the super-slices 100–103. If it is determined that the algorithm need not be reperformed, the model-based scatter correction method then proceeds to correct the full sinogram set, which is then used to generate scatter-corrected PET images. Whether or not the algorithm must be reperformed can be determined in a variety of ways, depending upon the embodiment. In one embodiment, a value is recorded, each time when the step 152 is performed, that is indicative of the difference between a current overall value of the corrected, normal-sized (and tail-scaled) sinogram of step 150 and a previous overall value of that sinogram. Further, at step 152, if the difference falls below a certain level, then it is determined that the scatter estimation as been iteratively performed a sufficient number of times.

As discussed, at step 148, the model-based scatter correction method computes the scatter contributions for the sinograms corresponding to the super-slices 100–103, and then further interpolates the sinograms so that the sinogram information is converted from information corresponding to the super-slices 100–103 to information corresponding to native axial slices 90. In one embodiment, the conversion of information from super-slice format to native axial slice format is made using the following equations:

$$s(i)=S(j) \quad i \leq j_0 \text{ or } i \geq j_N \quad (1)$$

$$s(i)=aS(j)+bS(j+1) \quad j<i<j+1 \quad (2)$$

In equations (1) and (2), s is the scatter in a particular (ith) native axial slice, S is the scatter estimate in a particular (jth) super-slice, $j_0$ is the location of the center of the first super-slice (e.g., the center 106 of the super-slice 100), $j_N$ is the location of the center of the last super-slice (e.g., the center 106 of the super-slice 103), and a and b are weighting factors determined by the relative distances from the native axial slice to the respective super-slice.

Equations (1) and (2) can thus be used to assign scatter contributions to each of the 2D native axial slices 90 from the corresponding 2D super-slices 100–103. Once all of the native axial slices (e.g., all thirty-five slices) are calculated, the scatter contributions to all of the oblique slices can then further be determined, where the oblique slices are within planes that are not perpendicular to the central axis 2. The scatter contributions to each oblique slice are made by determining which of the native axial slices corresponds to the location where the oblique slice crosses the central axis 2. Each oblique slice is then given a scatter contribution whose distribution is equal to that of its respective native axial slice but scaled using a method similar to that in step 139. Thus, scatter contributions need not be separately calculated for each oblique slice, but need only be calculated for the thirty-five 2D native axial slices 90.

It should be apparent to those skilled in the art that many modifications may be made from the embodiments disclosed herein without departing from the spirit and scope of the invention. For example, while 3D PET scanners having cylindrical detector ring assemblies are discussed above, it would also be possible to implement a similar method for estimating scatter in 3D PET scanners having detector ring assemblies of different shapes.

What is claimed is:

1. A method of processing an image data set of a 3D PET scanner to correct for scattered coincidence events, wherein the 3D PET scanner includes a detector ring assembly having a central axis, the method comprising:
   (a) providing an image data set including a first plurality of data subsets respectively corresponding to a plurality of native slices;
   (b) axially downsampling the first plurality of data subsets to generate a second plurality of data subsets respectively corresponding to a plurality of super-slices; and
   (c) calculating scatter in the second plurality of data subsets by way of a model-based scatter correction algorithm.

2. The method of claim 1, wherein the each of the plurality of native slices is an axial plane perpendicular to a central axis.

3. The method of claim 1, wherein each of the plurality of super-slices has an axial number and an axial extent, wherein the axial number of each super-slice refers to a number of the plurality of native slices that are encompassed within the respective super-slice, and the axial extent of each super-slice refers to a distance from a respective center of the respective super-slice.

4. The method of claim 3, wherein the axial extent is one of greater than, equal to, and less than a width corresponding to the axial number of native slices.

5. The method of claim 4, wherein the first image data set includes thirty-five data subsets corresponding to thirty-five native slices, and the second plurality of data subsets includes four data subset corresponding to four super-slices.

6. The method of claim 1, wherein the first image data set includes a 2D emission image set derived from a 3D set and a 2D transmission image set.

7. The method of claim 1, further comprising:
   (d) transaxially downsampling the second plurality of data subsets to generate a plurality of downsampled data subsets; and
   (e) converting the plurality of downsampled data subsets from an image format into a sinogram format to develop a downsampled sinogram data set.

8. The method of claim 7, wherein each of the second plurality of data subsets includes pixel information concerning a matrix of 128 by 128 pixels, and each of the plurality of downsampled data subsets includes pixel information concerning a matrix of 32 by 32 pixels.

9. The method of claim 7, wherein (e) includes calculating single scatter contributions and calculating multiple scatter contributions.

10. The method of claim 9, further comprising:
    (f) summing the single and multiple scatter contributions; and
    (g) interpolating the downsampled sinogram data set to arrive at a normal sinogram data set; and
    (h) setting the magnitude of the scatter contribution to the normal sinogram data set using tail scaling.

11. The method of claim 10, further comprising:
    (i) determining whether the scatter contribution, have been adequately determined; and
    (j) when the scatter contributions have not been adequately determined, repeating (d)–(i) and, when the scatter contributions have been adequately determined, proceeding to correct the modified normal sinogram data set.

12. The method of claim 10, wherein the interpolating of the downsampled data set includes converting data corresponding to the plurality of super-slices to data corresponding to the plurality of native slices.

13. The method of claim 10, wherein the converting of data proceeds according to the equations:

$$[s(i)=S(j)i \leq j_0 \text{ or } i \geq j_N]$$

and $$[s(i)=aS(j)+bS(j+1)j<i<j+1].$$

14. The method of claim 13, wherein a plurality of oblique slices are assigned scattering contributions equaling those of respective native axial slices that intersect the central axis at the same locations as the oblique slices intersect the central axis.

15. The method of claim 1, further comprising:
    initializing pre-calculated tables;

correcting 3D data of preliminary data set to generate the image data set, wherein the image data set includes an emission image data set and a transmission image data set; and computing sinogram boundaries relating to the image data set.

16. The method of claim 1, wherein the 3D PET scanner is one of a true-3D PET scanner and a pseudo-3D PET scanner.

17. A method of processing an image data set of a 3D PET scanner to correct for scattered coincidence events, wherein the 3D PET scanner includes a detector assembly having a central axis, the method comprising:

(a) providing an emission image data set and a transmission image data set, wherein the emission image data set includes a plurality of emission data subsets respectively corresponding to a plurality of native slices, and wherein the transmission image data set includes a plurality of transmission data subsets respectively corresponding to the plurality of native slices;

(b) axially downsampling the plurality of emission data subsets to generate an axially downsampled emission data set corresponding to at least one super-slice, and axially downsampling the plurality of transmission data subsets to generate an axially downsampled transmission data set corresponding to the at least one super-slice;

(c) transaxially downsampling each of the axially downsampled emission data set and the axially downsampled transmission data set to generate a downsampled emission data set and a downsampled transmission data set;

(d) calculating scatter based upon the downsampled emission and transmission data sets to generate a scatter sinogram data set; and (e) repeating (c)–(e) until scatter has been adequately calculated as determined according to a convergence rule.

18. A 3D PET scanner comprising:

a gantry;

a plurality of sets of detectors supported by the gantry, the detectors in each set being disposed in a plane and positioned about a central axis that intersects the plane, wherein the sets of detectors are spaced along the central axis, and wherein each set of detectors forms respective a native axial slice; and processor means for:

providing an image data set including a first plurality of data subsets respectively corresponding to the respective native slices;

axially downsampling the first plurality of data subsets to generate a second plurality of data subsets respectively corresponding to a plurality of super-slices; and calculating scatter in the second plurality of data subsets by way of a model-based scatter correction algorithm.

19. The 3D PET scanner of claim 18, wherein the scatter is iteratively calculated, and wherein the 3D PET scanner is one of a true-3D PET scanner and a pseudo-3D PET scanner.

20. The 3D PET scanner of claim 18, wherein the calculating of scatter includes transaxially downsampling the second plurality of data subsets, calculating single scatter contributions, and calculating multiple scatter contributions.

* * * * *